(12) United States Patent
Hunt et al.

(10) Patent No.: US 11,351,576 B2
(45) Date of Patent: Jun. 7, 2022

(54) DETERMINING ORE CHARACTERISTICS

(71) Applicant: X Development LLC, Mountain View, CA (US)

(72) Inventors: Thomas Peter Hunt, Oakland, CA (US); Neil David Treat, San Jose, CA (US); Karen R Davis, Portola Valley, CA (US); Artem Goncharuk, Mountain View, CA (US); Vikram Neal Sahney, Seattle, WA (US)

(73) Assignee: X Development LLC, Mountain View, CA (US)

( * ) Notice: Subject to any disclaimer, the term of this patent is extended or adjusted under 35 U.S.C. 154(b) by 0 days.

(21) Appl. No.: 16/892,861

(22) Filed: Jun. 4, 2020

(65) Prior Publication Data
US 2020/0384506 A1    Dec. 10, 2020

Related U.S. Application Data

(60) Provisional application No. 62/857,592, filed on Jun. 5, 2019.

(51) Int. Cl.
*B07C 5/34* (2006.01)
*B07C 5/342* (2006.01)
*B07C 5/344* (2006.01)
*B07C 5/346* (2006.01)
(Continued)

(52) U.S. Cl.
CPC ............ *B07C 5/3425* (2013.01); *B07C 5/344* (2013.01); *B07C 5/346* (2013.01); *B07C 5/3427* (2013.01);
(Continued)

(58) Field of Classification Search
CPC ..... B07C 5/3416; B07C 5/342; B07C 5/3425; B07C 5/3427; B07C 5/344; B07C 5/361;
(Continued)

(56) References Cited

U.S. PATENT DOCUMENTS

| 5,887,073 | A | * | 3/1999 | Fazzari | ................. | B07C 5/3422 |
| | | | | | | 382/110 |
| 8,553,838 | B2 | * | 10/2013 | Sommer | ................. | B07C 5/365 |
| | | | | | | 378/45 |

(Continued)

OTHER PUBLICATIONS

PCT International Search Report and Written Opinion in International Appln. No. PCT/US2020036065, dated Sep. 22, 2020, 17 pages.

(Continued)

*Primary Examiner* — Joseph C Rodriguez
(74) *Attorney, Agent, or Firm* — Fish & Richardson P.C.

(57) ABSTRACT

Techniques for processing ore include the steps of causing an imaging capture system to record a plurality of images of a stream of ore fragments en route from a first location in an ore processing facility to a second location in the ore processing facility; correlating the plurality of images of the stream of ore fragments with at least one or more characteristics of the ore fragments using a machine learning model that includes a plurality of ore parameter measurements associated with the one or more characteristics of the ore fragments; determining, based on the correlation, at least one of the one or more characteristics of the ore fragments; and generating, for display on a user computing device, data indicating the one or more characteristics of the ore fragments or data indicating an action or decision based on the one or more characteristics of the ore fragments.

34 Claims, 6 Drawing Sheets

(51) Int. Cl.
  *G01N 23/20091* (2018.01)
  *G01N 23/223* (2006.01)
  *G01N 23/207* (2018.01)
  *G01N 33/24* (2006.01)
  *G06N 3/08* (2006.01)
  *G06V 10/42* (2022.01)
  *G06V 20/00* (2022.01)

(52) U.S. Cl.
  CPC ..... *G01N 23/207* (2013.01); *G01N 23/20091* (2013.01); *G01N 23/223* (2013.01); *G01N 33/24* (2013.01); *G06N 3/08* (2013.01); *G06V 10/42* (2022.01); *G06V 20/00* (2022.01)

(58) Field of Classification Search
  CPC .............. B07C 5/346; G01N 23/20091; G01N 23/207; G01N 23/223; G01N 33/24
  See application file for complete search history.

(56) References Cited

U.S. PATENT DOCUMENTS

| | | | |
|---|---|---|---|
| 9,316,537 B2 * | 4/2016 | Bamber | B07C 5/3416 |
| 9,884,346 B2 * | 2/2018 | Bamber | B07C 5/08 |
| 10,493,494 B2 * | 12/2019 | Bamber | B07C 5/362 |
| 10,545,491 B2 * | 1/2020 | Kingston | G05B 19/41875 |
| 10,799,916 B2 * | 10/2020 | Shaw | B07C 5/361 |
| 11,021,801 B2 * | 6/2021 | Gomez | C25C 1/12 |
| 2003/0156739 A1 | 8/2003 | Hinton et al. | |
| 2007/0095168 A1 | 5/2007 | Vince et al. | |
| 2008/0192987 A1 | 8/2008 | Helgason et al. | |
| 2012/0125736 A1 | 5/2012 | Twigger et al. | |
| 2013/0026263 A1 * | 1/2013 | Bamber | G01N 27/025 241/24.1 |
| 2014/0088876 A1 * | 3/2014 | Shiley | G01N 21/359 702/8 |
| 2015/0078653 A1 | 3/2015 | Tafazoli Bilandi et al. | |
| 2018/0074481 A1 * | 3/2018 | Kingston | G06Q 20/22 |

OTHER PUBLICATIONS

Tripathy et al., "Multispectral and Joint Colour-Texture Feature Extraction for Ore-Gangue Separation," Pattern Recognition and Image Analysis, 2017, 27(2):338-348.

International Preliminary Report on Patentability in International Appln. No. PCT/US2020036065, dated Dec. 16, 2021, 10 pages.

* cited by examiner

DETERMINING ORE CHARACTERISTICS

CROSS-REFERENCE TO RELATED APPLICATION

This application claims priority under 35 U.S.C. § 119 to U.S. Provisional Patent Application Ser. No. 62/857,592, filed on Jun. 5, 2019, the entire contents of which are incorporated by reference herein.

TECHNICAL FIELD

This disclosure generally relates to determining ore characteristics and, more particularly, determining ore characteristics with one or more machine learning models.

BACKGROUND

Ore is processed through a complex series of steps such as, for example, comminution, sizing, concentration (such as froth flotation), electrostatic or magnetic separation. There are many variables that can be adjusted to improve the processing, based on the characteristics of the ore being processed.

SUMMARY

In general, the disclosure relates to using an imaging capture system to record video, or a series of still images of ore fragments as the fragments are en route from one location to another in an ore processing facility. The images of ore fragments are then used as input to a machine learning model, which can correlate characteristics of the ore in the images with one or more parameter measurements associated with the characteristics of the ore, and determine the characteristics of the ore that is being imaged. These determined characteristics can then be readily displayed to a user on a computing device, or used as input to change an operating parameter or mode of operation of the processing facility. In one implementation the system can detect anomalous pieces of ore, and stop a conveyor belt, to allow for further inspection, or to prevent damage to equipment.

In general, innovative aspects of the subject matter described in this specification can be embodied in methods that include the actions of using a machine learning model to determine characteristics of ore in an ore processing facility. Other implementations of this aspect include corresponding systems, apparatus, and computer programs, configured to perform the actions of the methods, encoded on computer storage devices.

In an example implementation, an ore processing system includes one or more processors; one or more tangible, non-transitory media operably connectable to the one or more processors and storing instructions that, when executed, cause the one or more processors to perform operations. The operations include causing an imaging capture system to record a plurality of images of a stream of ore fragments en route from a first location in an ore processing facility to a second location in the ore processing facility; correlating the plurality of images of the stream of ore fragments with one or more characteristics of the ore fragments using a machine learning model that includes a plurality of ore parameter measurements associated with the one or more characteristics of the ore fragments; determining, based on the correlation, at least one of the one or more characteristics of the ore fragments; and generating, for display on a user computing device, data indicating the one or more characteristics of the ore fragments or data indicating an action or decision based on the one or more characteristics of the ore fragments.

In an aspect combinable with the example implementation, the plurality of images include images including layers of red, green, blue, and grey; hyperspectral images; acoustic images; gravimetric images; or depth imagery images.

In an aspect combinable with any one of the previous aspects, the machine learning model includes an artificial neural network.

In an aspect combinable with any one of the previous aspects, the plurality of ore parameter measurements include measurements based on at least one of x-ray diffraction (XRD), x-ray fluorescence (XRF), or energy dispersive x-ray (EDS).

In an aspect combinable with any one of the previous aspects, the one or more characteristics includes at least one of mineral composition, density, porosity, fracture type, fragment size, fragment moisture content, or hardness.

In an aspect combinable with any one of the previous aspects, the operations further include based on the determined one or more characteristics of the ore fragments, adjusting an operation of the ore processing facility.

In an aspect combinable with any one of the previous aspects, adjusting an operation of the ore processing facility includes at least one of causing a change of route of the stream of ore fragments from the first location in the ore processing facility to a third location in the ore processing facility different than the second location; causing a change to an ore processing parameter in the ore processing facility; or causing an adjustment of an ore source of the stream of ore fragments moving through the ore processing facility.

In an aspect combinable with any one of the previous aspects, causing a change to an ore processing parameter in the ore processing facility includes causing a change to a chemical composition of a froth flotation system of the ore processing facility.

An aspect combinable with any one of the previous aspects further includes an electromagnetic (EM) imaging system.

In an aspect combinable with any one of the previous aspects, the operations further include causing the EM imaging system to record a plurality of EM images of the stream of ore fragments moving from the first location in the ore processing facility to the second location in the ore processing facility; and determining, based on the plurality of EM images, one or more mineral characteristics of the ore fragments.

In an aspect combinable with any one of the previous aspects, the one or more mineral characteristics includes at least one of ore fragment density, ore fragment size, or ore fragment surface composition.

In an aspect combinable with any one of the previous aspects, the operations further include determining, based on at least one of the plurality of images, an anomaly within the stream of ore fragments; and based on the determination of the anomaly, causing a change to an operation of the ore processing facility.

In an aspect combinable with any one of the previous aspects, the change to the operation of the ore processing facility includes causing a stop to a movement of the stream of ore fragments en route from the first location in the ore processing facility to the second location in the ore processing facility.

In an aspect combinable with any one of the previous aspects, causing the imaging capture system to record the plurality of images of the stream of ore fragments en route from the first location in the ore processing facility to the second location in the ore processing facility includes causing the imaging capture system to record the plurality of images of the stream of ore fragments as the ore fragments are moving from the first location in the ore processing facility to the second location in the ore processing facility.

In an aspect combinable with any one of the previous aspects, causing the imaging capture system to record the plurality of images of the stream of ore fragments as the ore fragments are moving from the first location in the ore processing facility to the second location in the ore processing facility includes causing the imaging capture system to record the plurality of images of the stream of ore fragments as the ore fragments are moving on a conveyor or belt continuous feed system from the first location in the ore processing facility to the second location in the ore processing facility.

In an aspect combinable with any one of the previous aspects, the machine learning model is trained on a data corpus that includes a plurality of ore fragment samples measured by at least one of x-ray diffraction (XRD), x-ray fluorescence (XRF), or energy dispersive x-ray (EDS) to correlate a plurality of ore parameter measurements of the ore fragment samples with at least one ore fragment characteristic of the ore fragment samples.

In an aspect combinable with any one of the previous aspects, the trained machine learning model is retrainable based on at least one of: a change in source location of the ore fragments in the stream of ore fragments, or a change in geological location of the ore fragments in the stream of ore fragments.

In an aspect combinable with any one of the previous aspects, the ore fragments are pretreated with an imaging enhancement prior to the recording of the plurality of images.

In another example implementation, a computer-implemented ore processing method executed by one or more processors includes causing an imaging capture system to record a plurality of images of a stream of ore fragments en route from a first location in an ore processing facility to a second location in the ore processing facility; correlating the plurality of images of the stream of ore fragments with at least one or more characteristics of the ore fragments using a machine learning model that includes a plurality of ore parameter measurements associated with the one or more characteristics of the ore fragments; determining, based on the correlation, at least one of the one or more characteristics of the ore fragments; and generating, for display on a user computing device, data indicating the one or more characteristics of the ore fragments or data indicating an action or decision based on the one or more characteristics of the ore fragments.

In an aspect combinable with the example implementation, the plurality of images include images including layers of red, green, blue, and grey; hyperspectral images; acoustic images; gravimetric images; or depth imagery images.

In an aspect combinable with any one of the previous aspects, the machine learning model includes an artificial neural network.

In an aspect combinable with any one of the previous aspects, the plurality of ore parameter measurements include measurements based on at least one of x-ray diffraction (XRD), x-ray fluorescence (XRF), or energy dispersive x-ray (EDS).

In an aspect combinable with any one of the previous aspects, the one or more characteristics includes at least one of mineral composition, density, porosity, or hardness.

An aspect combinable with any one of the previous aspects further includes based on the determined one or more characteristics of the ore fragments, adjusting an operation of the ore processing facility.

In an aspect combinable with any one of the previous aspects, adjusting an operation of the ore processing facility includes at least one of causing a change of route of the stream of ore fragments from the first location in the ore processing facility to a third location in the ore processing facility different than the second location; causing a change to an ore processing parameter in the ore processing facility; or causing an adjustment of an ore source of the stream of ore fragments moving through the ore processing facility.

In an aspect combinable with any one of the previous aspects, causing a change to an ore processing parameter in the ore processing facility includes causing a change to a chemical composition of a froth flotation system of the ore processing facility.

An aspect combinable with any one of the previous aspects further includes causing an electromagnetic (EM) imaging system to record a plurality of EM images of the stream of ore fragments moving from the first location in the ore processing facility to the second location in the ore processing facility; determining, based on the plurality of EM images, one or more mineral characteristics of the ore fragments.

In an aspect combinable with any one of the previous aspects, the one or more mineral characteristics includes at least one of ore fragment density, ore fragment size, or ore fragment surface composition.

An aspect combinable with any one of the previous aspects further includes determining, based on at least one of the plurality of images, an anomaly within the stream of ore fragments; and based on the determination of the anomaly, causing a change to an operation of the ore processing facility.

In an aspect combinable with any one of the previous aspects, the change to the operation of the ore processing facility includes causing a stop to movement of the ore stream en route from the first location in the ore processing facility to the second location in the ore processing facility.

In an aspect combinable with any one of the previous aspects, causing the imaging capture system to record the plurality of images of the stream of ore fragments en route from the first location in the ore processing facility to the second location in the ore processing facility includes causing the imaging capture system to record the plurality of images of the stream of ore fragments as the ore fragments are moving from the first location in the ore processing facility to the second location in the ore processing facility.

In an aspect combinable with any one of the previous aspects, causing the imaging capture system to record the plurality of images of the stream of ore fragments as the ore fragments are moving from the first location in the ore processing facility to the second location in the ore processing facility includes causing the imaging capture system to record the plurality of images of the stream of ore fragments as the ore fragments are moving on a conveyor or belt continuous feed system from the first location in the ore processing facility to the second location in the ore processing facility.

In an aspect combinable with any one of the previous aspects, the machine learning model is trained on a data corpus that includes a plurality of ore fragment samples measured by at least one of x-ray diffraction (XRD), x-ray fluorescence (XRF), or energy dispersive x-ray (EDS) to correlate a plurality of ore parameter measurements of the ore fragment samples with at least one ore fragment characteristic of the ore fragment samples.

In an aspect combinable with any one of the previous aspects, the trained machine learning model is retrainable based on at least one of: a change in source location of the ore fragments in the stream of ore fragments, or a change in geological location of the ore fragments in the stream of ore fragments.

In an aspect combinable with any one of the previous aspects, the ore fragments are pretreated with an imaging enhancement prior to the recording of the plurality of images.

In another example implementation, a non-transitory computer readable storage medium storing instructions that, when executed by at least one processor, cause the at least one processor to perform operations that include causing an imaging capture system to record a plurality of images of a stream of ore fragments en route from a first location in an ore processing facility to a second location in the ore processing facility; correlating the plurality of images of the stream of ore fragments with at least one or more characteristics of the ore fragments using a machine learning model that includes a plurality of ore parameter measurements associated with the one or more characteristics of the ore fragments; determining, based on the correlation, at least one of the one or more characteristics of the ore fragments; and generating, for display on a user computing device, data indicating the one or more characteristics of the ore fragments or data indicating an action or decision based on the one or more characteristics of the ore fragments.

In another example implementation, an ore processing system includes one or more processors; and one or more tangible, non-transitory media operably connectable to the one or more processors and storing instructions that, when executed, cause the one or more processors to perform operations. The operations include causing an optical imaging capture system to record a plurality of images of a stream of ore fragments en route from a first location in an ore processing facility to a second location in the ore processing facility; correlating the plurality of images of the stream of ore fragments with at least one or more characteristics of the ore fragments using a machine learning model that includes a plurality of ore parameter measurements associated with the one or more characteristics of the ore fragments; determining, based on the correlation, at least one of the one or more characteristics of the ore fragments; and generating, for display on a user computing device, data indicating the one or more characteristics of the ore fragments or data indicating an action or decision based on the one or more characteristics of the ore fragments.

The details of one or more implementations of the subject matter of this disclosure are set forth in the accompanying drawings and the description below. Other features, aspects, and advantages of the subject matter will become apparent from the description, the drawings, and the claims.

DETAILED DESCRIPTION

Figure 1A:
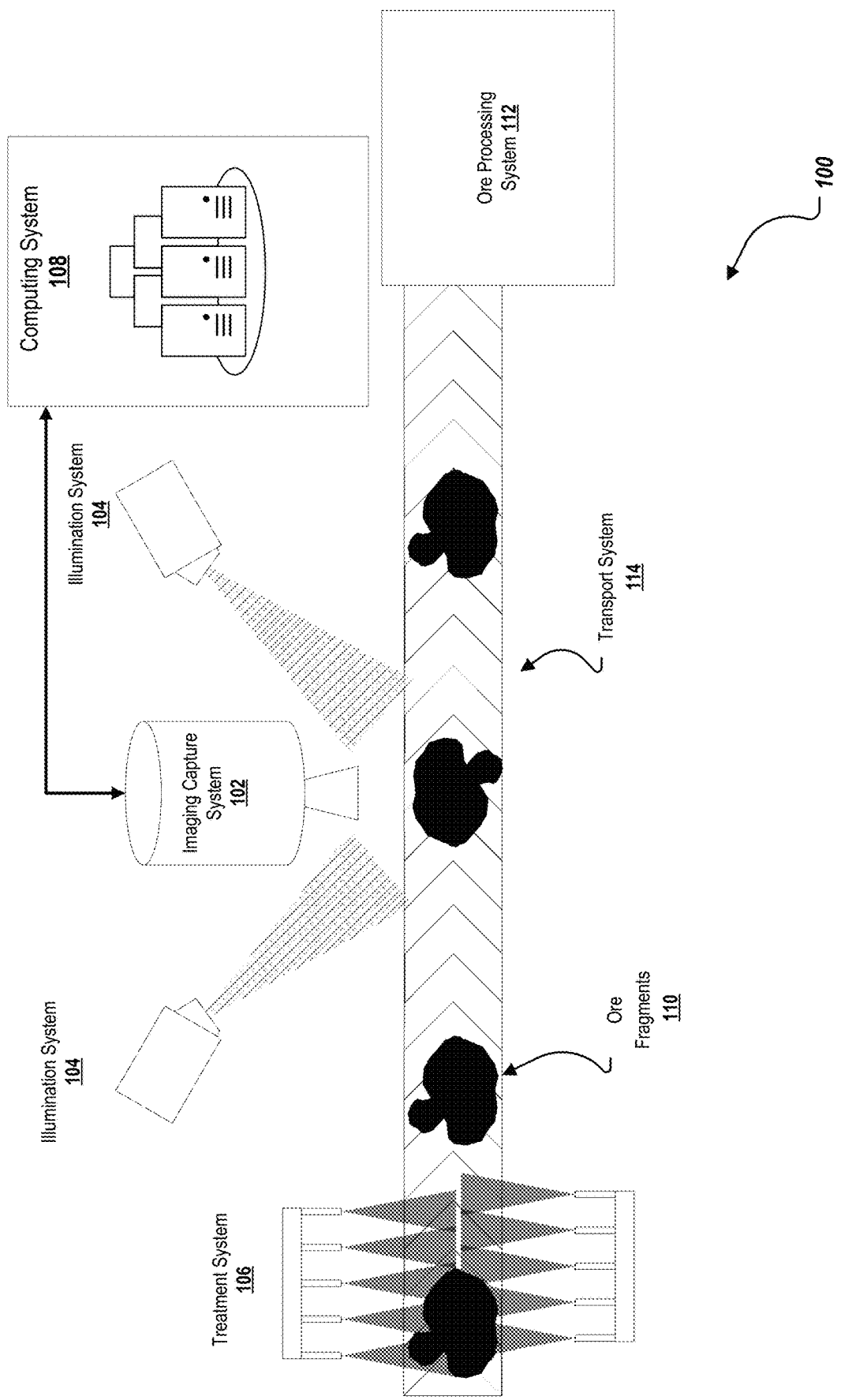
FIG. 1A depicts an example implementation of at least a portion of an ore processing facility that includes an ore composition imaging system.

FIG. 1A depicts an example implementation of at least a portion of an ore processing facility 100. The system 100 can be integrated into a conventional ore processing facility, or at a mining facility, or any other suitable location. In a typical ore processing facility ore transported from the mine must be processed to separate valuable minerals. This process often includes comminution, or the reduction of fragment size on the material. This is often done via crushing or grinding. Then the ore is sorted according to size, and concentrated. Concentration refers to increasing the concentration of valuable minerals in a given stream of ore. Concentration can occur via several methods (e.g., gravity concentration, froth flotation, electrostatic separation, or magnetic separation).

In one implementation the ore composition imaging system 100 is integrated after the ore is initially crushed, while it is being transported for further processing. The ore composition imaging system 100 can include an image capture system 102, which records video and/or still images of ore fragments 110 as they travel between two locations in an ore processing facility. The images from the image capture system can then be used as input to a computing system 108 that includes a machine learning model. The machine learning model can determine, using measured parameters of the ore fragments 110 ore characteristics, which can be used to adjust or modify the operation of the processing facility. The ore composition imaging system 100 can optionally include an illumination system 104, which can enhance the images captured by the image capture system 102, and a treatment system 106, which can treat the ore to further enhance the images.

The mineral composition imaging system 100 includes an image capture system 102, which captures image data of ore fragments 110 as they travel past the image capture system 102. The image data can include, but is not limited to, optical image data, hyperspectral images, x-ray images, acoustic images, electro-magnetic images, gravimetric images, electromagnetic (EM) images, or depth imagery images such as LIDAR, RADAR, or stereoscopic images.

For example, in one implementation the image capture system 102 captures high definition red, green, blue (RGB) video, which can be captured by a commercial video camera. In another implementation, the image capture system 102 can be an array of complementary metal oxide-semiconductor (CMOS) sensors, or charge-coupled devices (CCD's). In this implementation, the image capture system 102 can capture image data associated with images over a range of wavelengths broader than visible light, for example, 300 nm to 1000 nm. These images captured over a broad range of wavelengths can constitute hyperspectral images.

In some instances an illumination system 104 may be used to enhance the images captured by the image capture system 102. The illumination system 104 can emit visible light, ultra violet (UV) light, infra-red (IR) light, x-ray radiation, radio-frequency (RF) radiation, or any combination thereof, as well as any other suitable radiation for improving the image captured by the image capture system 102.

The image capture system 102 can then send image data to the computing system 108. The computing system 108 processes the image data to determine at least one characteristic of the ore fragments 110. The computing system 108 can include a machine learning model, for example a neural network, the machine learning model can be trained to detect patterns based on the image data and determine characteristics of the ore fragments 110. The machine learning model can do this based on correlating parameters measured in the ore fragments 110 and parameters of known previous measurements or ore. This provides the computing system 108 with the ability to perform accurate pattern recognition, automatically, or with minimal user input once the system is properly trained. For example, the machine learning model can determine the mineral composition, density, porosity, fracture type, fragment size, moisture content, surface composition, and hardness, among other things.

The ore fragments 110 are transported throughout the ore processing facility as they undergo various processing steps. The ore can be transported via a number of techniques, such as conveyor belt, train/cart and rail, barges, or slurry pipelines. The transport system 114 depicted in FIG. 1A is depicted as a conveyor belt; the present disclosure is not limiting thereto. The mineral composition imaging system 100 can be used in conjunction with any combination of transport system 114.

In one implementation, the mineral composition imaging system 100 includes a treatment system 106. The treatment system 106 can spray the ore fragments with a treatment solution prior to the ore being imaged. The treatment solution can enhance the captured images received by the image capture system 102. The treatment can include, but is not limited to, water, acid, non-penetrant dye, or a fluorescence enhancing solution.

In an example operation of the mineral composition imaging system 100, ore fragments 110 may be, for example, places on a transport system 114 after being comminuted and before sizing or concentration. The ore fragments 110 may be brought to the transport system 114 from a separate facility, such as a mining facility, or a comminution facility. The ore fragments 110 can then be treated using the treatment system 106 which can spray the ore fragments 110 with, for example, an acid mixture, to remove external impurities and enhance the ore for imaging. Following treatment the ore passes by the image capture system 102, which records a series of images of the ore stream as the ore fragments 110 pass by. The images are then processed by a computing system 108 which correlates parameters measured in the ore from the images with parameters contained in a machine learning model, and are associated with ore characteristics. The computing system 108 can then determine at least one characteristic about the ore passing by the image capture system 102. For example, the mineral composition for the ore, among other things. Based on the output of the computing system 108 the ore processing facility can adjust a parameter to optimize the processing of the ore. In some examples, the ore processing facility may change the addition rate of flotation reagents in a froth flotation processes, to compensate for a change in mineral composition of the incoming ore stream. Alternatively the processing facility may cause another change to the chemical composition of the froth flotation system. In another instance, the computing system 108 can detect an anomaly in the transport system 114. For example, a tool or piece of equipment dropped onto a conveyor belt. In this instance the ore processing facility can stop the belts, preventing potential damage, or loss of equipment.

Figure 1B:
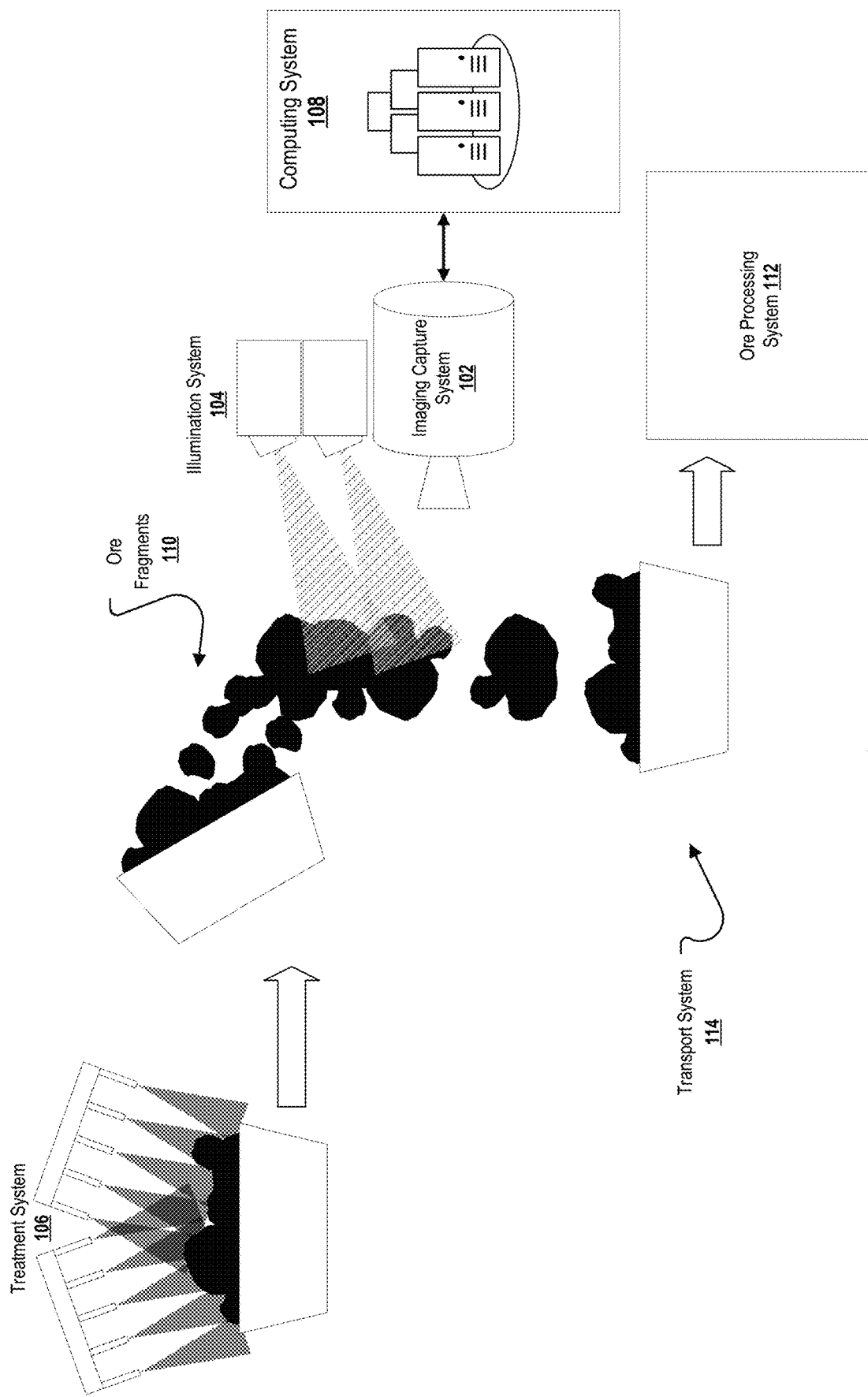
FIG. 1B depicts another example implementation of at least a portion of an ore processing facility that includes an ore composition imaging system.

FIG. 1B depicts another example implementation of at least a portion of an ore processing facility 100. The system 100 can be integrated into a conventional ore processing facility, or at a mining facility, or any other suitable location. In a typical ore processing facility ore transported from the mine must be processed to separate valuable minerals. This process often includes comminution, or the reduction of fragment size on the material. This is often done via crushing or grinding. Then the ore is sorted according to size, and concentrated. Concentration refers to increasing the concentration of valuable minerals in a given stream of ore. Concentration can occur via several methods (e.g., gravity concentration, froth flotation, electrostatic separation, magnetic separation)

In one implementation the ore composition imaging system 100 is integrated after the ore is initially crushed, while it is being transported for further processing. The ore composition imaging system 100 can include an image capture system 102, which records video and/or still images of ore fragments 110 as they travel between two locations in an ore processing facility. The images from the image capture system can then be used as input to a computing system 108 that includes a machine learning model. The machine learning model can determine, using measured parameters of the ore fragments 110 ore characteristics, which can be used to adjust or modify the operation of the processing facility. The ore composition imaging system 100 can optionally include an illumination system 104, which can enhance the images captured by the image capture system 102, and a treatment system 106, which can treat the ore to further enhance the images.

The mineral composition imaging system 100 includes an image capture system 102, which captures image data of ore fragments 110 as they travel past the image capture system 102. The image data can include, but is not limited to, optical image data, hyperspectral images, x-ray images, acoustic images, electro-magnetic images, gravimetric images, electromagnetic (EM) images, or depth imagery images such as LIDAR, RADAR, or stereoscopic images.

For example, in one implementation the image capture system 102 captures high definition red, green, blue (RGB) video, which can be captured by a commercial video camera. In another implementation, the image capture system 102 can be an array of complementary metal oxide-semiconductor (CMOS) sensors, or charge-coupled devices (CCD's). In this implementation, the image capture system 102 can capture image data associated with images over a range of wavelengths broader than visible light, for example, 300 nm to 1000 nm. These images captured over a broad range of wavelengths can constitute hyperspectral images.

In some instances an illumination system 104 may be used to enhance the images captured by the image capture system 102. The illumination system 104 can emit visible light, ultra violet (UV) light, infra-red (IR) light, x-ray radiation, radio-frequency (RF) radiation, or any combination thereof, as well as any other suitable radiation for improving the image captured by the image capture system 102.

The image capture system 102 can then send image data to the computing system 108. The computing system 108 processes the image data to determine at least one characteristic of the ore fragments 110. The computing system 108 can include a machine learning model, for example a neural network, the machine learning model can be trained to detect patterns based on the image data and determine characteristics of the ore fragments 110. The machine learning model can do this based on correlating parameters measured in the ore fragments 110 and parameters of known previous measurements or ore. This provides the computing system 108 with the ability to perform accurate pattern recognition, automatically, or with minimal user input once the system is properly trained. For example, the machine learning model can determine the mineral composition, density, porosity, fracture type, fragment size, moisture content, surface composition, and hardness, among other things.

The ore fragments 110 are transported throughout the ore processing facility as they undergo various processing steps. The ore can be transported via a number of techniques, such as conveyor belt, train/cart and rail, barges, or slurry pipelines. The transport system 114 depicted in FIG. 1B is shown as ore fragments being poured from one cart to another, or freefalling; the present disclosure is not limiting thereto. The mineral composition imaging system 100 can be used in conjunction with any combination of transport system 114.

In one implementation, the mineral composition imaging system 100 includes a treatment system 106. The treatment system 106 can spray the ore fragments with a treatment solution prior to the ore being imaged. The treatment solution can enhance the captured images received by the image capture system 102. The treatment can include, but is not limited to, water, acid, non-penetrant dye, or a fluorescence enhancing solution.

In an example operation of the mineral composition imaging system 100, ore fragments 110 may be, for example, places on a transport system 114 after being comminuted and before sizing or concentration. The ore fragments 110 may be brought to the transport system 114 from a separate facility, such as a mining facility, or a comminution facility. The ore fragments 110 can then be treated using the treatment system 106 which can spray the ore fragments 110 with, for example, an acid mixture, to remove external impurities and enhance the ore for imaging. Following treatment the ore passes by the image capture system 102, which records a series of images of the ore stream as the ore fragments 110 pass by. The images are then processed by a computing system 108 which correlates parameters measured in the ore from the images with parameters contained in a machine learning model, and are associated with ore characteristics. The computing system 108 can then determine at least one characteristic about the ore passing by the image capture system 102. For example, the mineral composition for the ore, among other things. Based on the output of the computing system 108 the ore processing facility can adjust a parameter to optimize the processing of the ore. In one instance, the ore processing facility may change the addition rate of flotation reagents in a froth flotation processes, to compensate for a change in mineral composition of the incoming ore stream. Alternatively the processing facility may cause another change to the chemical composition of the froth flotation system. In another instance, the computing system 108 can detect an anomaly in the transport system 114. For example, a tool or piece of equipment dropped onto a conveyor belt. In this instance the ore processing facility can stop the belts, preventing potential damage, or loss of equipment.

Figure 2:
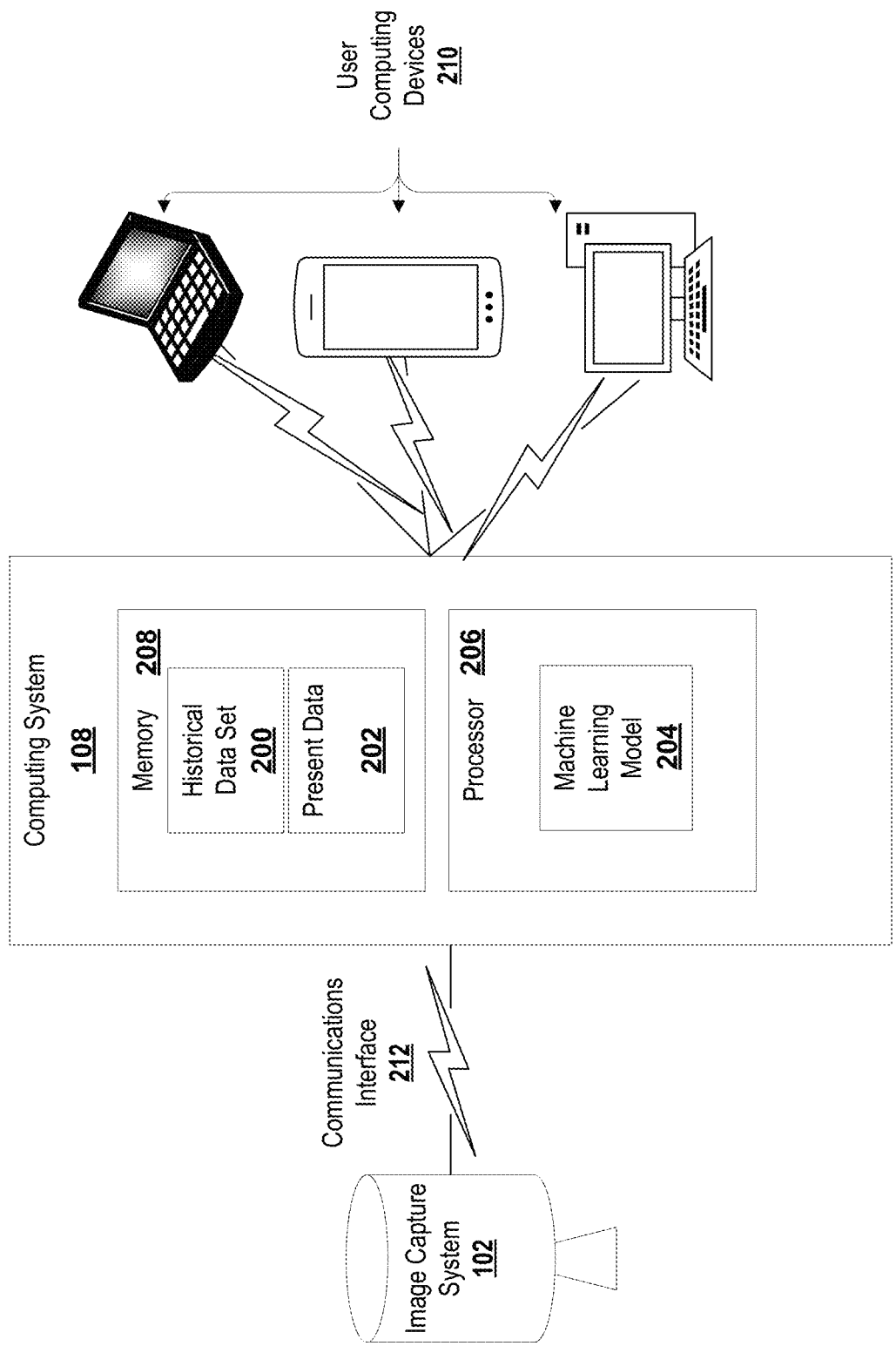
FIG. 2 depicts a computing system with a machine learning model for analyzing images of ore fragments.

FIG. 2 depicts an implementation of a computing system 108. In some implementations, the machine learning model 204 (or portions thereof) can be executed by the image capture system 102. In some examples, operations of the machine learning model 204 can be distributed between the image capture system 102 and the computing system 108.

The computing system 108 receives present data 202 from the image capture system 102 via the communications interface 212. The computing system 108 can also receive present data 202 from other user computing devices 210, or a network. In some implementations the present data can be received in real-time. The present data 202 is then used by the machine learning model 204 to generate an output determining one or more characteristics of the ore fragments 110. The present data 202 can include one of, or any combination of measured parameters of the ore fragments 110. These measured parameters can be determined from, for example, x-ray diffraction (XRD), x-ray fluorescence (XRF), energy dispersive x-ray (EDS), and can be reflectivity, color, geometry, or imperfection density, among other things.

Characteristics of ore fragments 110 can include, but are not limited to, mineral composition, density, porosity, fracture type, fragment size, fragment moisture content, surface composition, or hardness, among other things.

The machine learning model 204 may also accept as input operational parameters of the facility. These parameters can include, but are not limited to, belt speed, ore transport rate, ore fragment 110 size, time of day, or origin location of the ore. Facility parameters may be obtained via a manual input, or by additional sensors on the throughout the facility, among other things.

The computing system 108 can store in memory a historical data set 200 for a particular facility. The historical data set can include all data that has previously been used, or a subset of the previous data. The historical data set 202 can also include data relating to common trends seen across multiple facilities, among other things.

The machine learning model 204 receives the present data 202, and the historical data 200 and generates an output. For example, the machine learning model 204 can compare the present data (e.g., present x-ray fluorescence) with historical data (e.g., historical x-ray fluorescence for a known ore composition) to identify changes in the ore composition as the ore fragments 110 pass the imaging capture system 102. For example, the machine learning model 204 can identify, a concentration of a particular metal as it passes through the ore processing facility. The machine learning model 204 can correlate the detected changes in the ore fragment parameters with known patterns of ore fragment parameter (e.g., a library of ore fragment images containing known characteristics) to generate an output describing the ore fragments 110 passing through the ore processing facility. The output can include, but is not limited to a measurement of mineral composition, density, porosity, fracture type, fragment size, fragment moisture content, surface composition, or hardness, among other things.

Upon determining one or more characteristics of the ore fragments 110, the computing system 108 can provide a signal to alter one or more operations in the ore processing facility. In one implementation, the computing system 108 can simply provide for display on a user computing device 210, the determined characteristics. In another implementation the computing system 108 can adjust the route of the ore fragments 110 (e.g., activate a different belt or open a chute to a new hopper), allowing ore to be sent to a specific location in the processing facility, to be processed. In yet another implementation, the computing system 108 can make an adjustment to a parameter in the ore processing facility, for example, the computing system 108 can signal to increase the addition rate of flotation reagents in a froth flotation processes, in response to determining the ore fragments 110 are changing density, or mineral composition.

Additionally the computer system 108 can signal to change the speed of the transport system 114, or stop it altogether, in response to a detected characteristic in the ore fragments 110.

In some implementations, the machine learning model 204 incorporates additional data such as environmental factors associated with the facility (e.g., weather, temperature, time of day, date, or location). For example, the machine learning model 204 can correlate the identified changes in the ore fragments, with the environmental factors to assist in deterring one or more ore characteristics.

In some implementations, the machine learning model 204 is a deep learning model that employs multiple layers of models to generate an output for a received input. A deep neural network is a deep machine learning model that includes an output layer and one or more hidden layers that each apply a non-linear transformation to a received input to generate an output. In some cases, the neural network may be a recurrent neural network. A recurrent neural network is a neural network that receives an input sequence and generates an output sequence from the input sequence. In particular, a recurrent neural network uses some or all of the internal state of the network after processing a previous input in the input sequence to generate an output from the current input in the input sequence. In some other implementations, the machine learning model 204 is a convolutional neural network. In some implementations, the machine learning model 204 is an ensemble of models that may include all or a subset of the architectures described above.

In some implementations, the machine learning model 204 can be a feedforward autoencoder neural network. For example, the machine learning model 204 can be a three-layer autoencoder neural network. The machine learning model 204 may include an input layer, a hidden layer, and an output layer. In some implementations, the neural network has no recurrent connections between layers. Each layer of the neural network may be fully connected to the next, e.g., there may be no pruning between the layers. The neural network may include an optimizer for training the network and computing updated layer weights, such as, but not limited to, ADAM, Adagrad, Adadelta, RMSprop, Stochastic Gradient Descent (SGD), or SGD with momentum. In some implementations, the neural network may apply a mathematical transformation, e.g., a convolutional transformation or factor analysis to input data prior to feeding the input data to the network.

In some implementations, the machine learning model 204 can be a supervised model. For example, for each input provided to the model during training, the machine learning model 204 can be instructed as to what the correct output should be. The machine learning model 204 can use batch training, e.g., training on a subset of examples before each adjustment, instead of the entire available set of examples. This may improve the efficiency of training the model and may improve the generalizability of the model. The machine learning model 204 may use folded cross-validation. For example, some fraction (the "fold") of the data available for training can be left out of training and used in a later testing phase to confirm how well the model generalizes. In some implementations, the machine learning model 204 may be an unsupervised model. For example, the model may adjust itself based on mathematical distances between examples rather than based on feedback on its performance.

A machine learning model 204 can be trained to recognize patterns in a stream of ore fragments 110 when compared with the historical data, including images of ore fragments, and environmental parameters. In some examples, the machine learning model 204 can be trained on hundreds of recorded images of ore fragments. The machine learning model 204 can be trained to identify specific characteristics of the ore fragments, or potential anomalies in the fragment stream.

The machine learning model 204 can be, for example, a deep-learning neural network or a "very" deep-learning neural network. For example, the machine learning model 204 can be a convolutional neural network. The machine learning model 204 can be a recurrent network. The machine learning model 204 can have residual connections or dense connections. The machine learning model 204 can be an ensemble of all or a subset of these architectures. The machine learning model 204 is trained to determine one or more characteristics of the ore fragments 110 passing by the image capture system 102 based on detecting patterns from one or more of the present data 202 and the historical data set 200. The model may be trained in a supervised or unsupervised manner. In some examples, the model may be trained in an adversarial manner. In some examples, the model may be trained using multiple objectives, loss functions or tasks.

The machine learning model 204 can be configured to provide a binary output, e.g., a yes or no indication of whether an anomaly is present in the ore stream. In some examples, the machine learning model 204 is configured to determine multiple ore characteristics and a certainty rating for each characteristic. For example, based on the present and historical data, the machine learning model can determine that ore fragments have a 2% concentration of zinc, with a 70% certainty rating.

Figure 3:
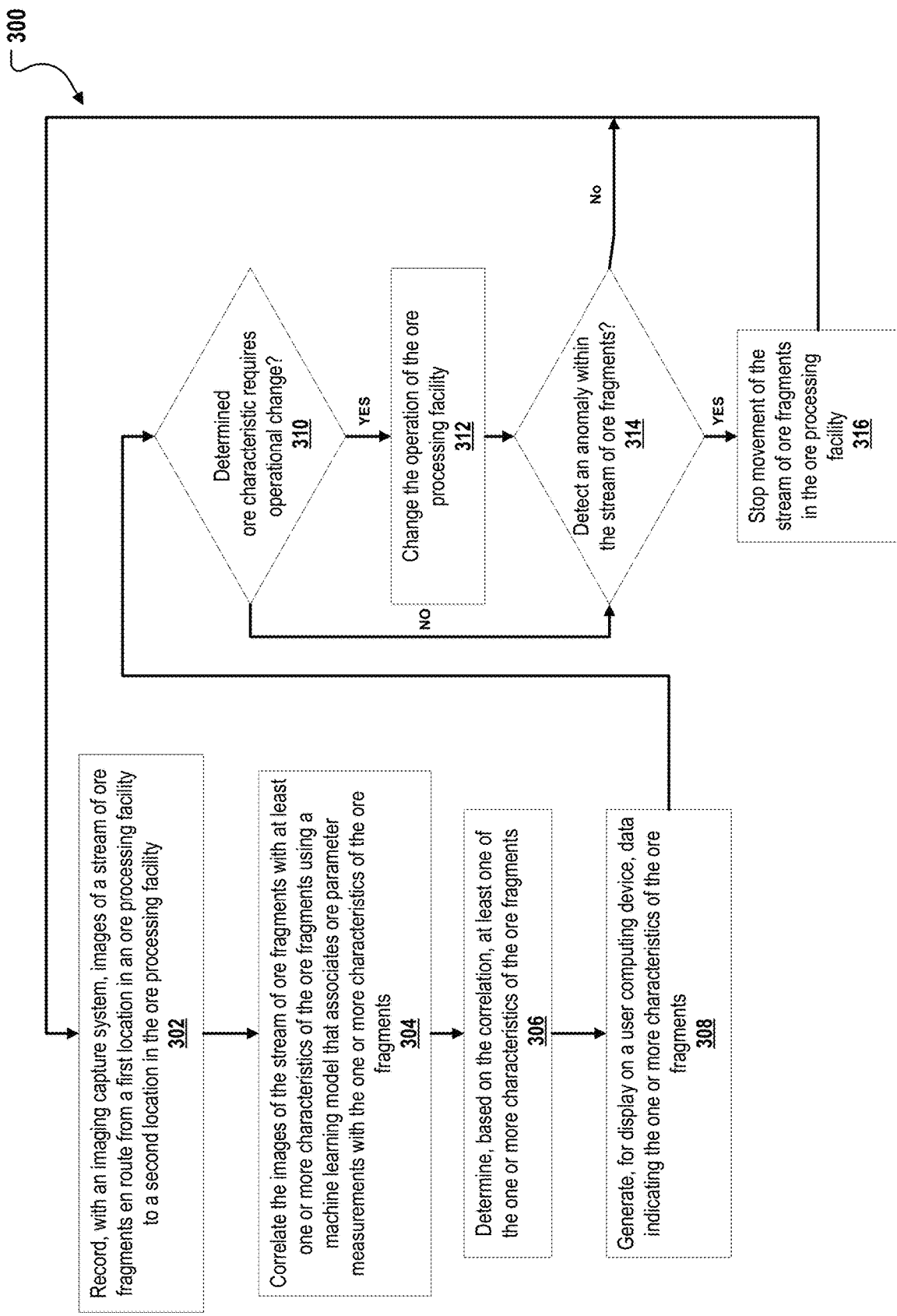
FIG. 3 is a flowchart illustrating an example method for determining characteristics of ore, and altering a processing facilities operation based on the determination.

FIG. 3 is a flowchart illustrating an example method for determining characteristics of ore, and altering a processing facilities operation based on the determination. For clarity of presentation, the description that follows generally describes method 300 in the context of the other figures in this description. However, it will be understood that method 300 can be performed, for example, by any system, environment, software, and hardware, or a combination of systems, environments, software, and hardware, as appropriate. In some implementations, various steps of method 300 can be run in parallel, in combination, in loops, or in any order.

Method 300 can begin at 302. An image capture system 102 records images of a stream of ore fragments 110 as they travel between two locations in an ore processing facility. The images recorded can be, but are not limited to optical RGB recordings, hyperspectral scans, x-ray images, electromagnetic images, acoustic images, gravimetric images, or depth imagery images. In one implementation, the images are x-ray diffraction (XRD) images. In another implementation the images can be x-ray fluorescence (XRF), and can indicate the presence or concentrations of specific minerals in the ore. In yet another implementation the images are energy dispersive x-rays (EDS). The foregoing are example implementations, the present disclosure is not limited thereto. From 302 method 300 proceeds to 304.

At 304 the images of the stream of ore fragments are correlated with one or more characteristics of the ore fragments. The correlation can be accomplished using a machine learning model as described above. The machine learning model can associate one or more parameter measurements from the images with one or more characteristics of the ore fragments and correlate for example, ore mineral composition, density, porosity, fracture type, fragment size, fragment moisture content, surface composition, or hardness, among other things. Method 300 then proceeds to 306.

At 306 the computing system 108 determines, based on the correlation, one or more characteristics of the ore fragments. These characteristics can be the output of the machine learning model 204.

At 308 the one or more characteristics determined at 306 are displayed on a user computing device 210. The user computing device 210 can be a laptop, personal computer, cell phone, tablet, or any suitable device with a display. For example, the computing system 108 can determine the mineral composition and fragment moisture content, and display this information, along with a certainty measurement on a plant manager's cell phone, or a local control computer inside the ore processing facility. The determined characteristics can be fed as an input to another system as well.

At 310 a determination is made whether an operational change is required in the ore processing facility, based on the determined characteristics. If it is determined that a change is required, method 300 proceeds to step 312. If it is determined that no change is required, method 300 proceeds to step 314.

At 312, the operation of the ore processing facility is changed based on the determined characteristics of the ore. For example, if it is determined that the total mass of the ore fragments has increased, belt speed can be increased, and additional processing facilities can be activated to accommodate the increased throughput. In another example, if it is determined that the mineral composition has changed, the transport system 114 can be rerouted to a different processing system in the ore processing facility. In yet another example, the ore processing facility may change the addition rate of flotation reagents in a froth flotation processes, to compensate for a change in mineral composition of the incoming ore stream. Alternatively the processing facility may cause a different change to the chemical composition of the froth flotation system. Following step 312 method 300 proceeds to 314.

At 314 a determination is made as to whether or not there is an anomaly in the stream of ore fragments 110. An anomaly can be, for example, a tool or piece of equipment in the ore belt, or an oversize fragment, among other things. If it is determined that no anomaly is present, method 300 returns to 302, and continues normal operations. If it is determined that there is an anomaly present, method 300 proceeds to 316.

At 316 the computing system 108 can send a signal to stop the transport system 114 and cease movement of ore in the processing facility. This can allow operators to investigate the anomaly or remove it as necessary, preventing potential damage or loss of equipment. Following investigation of the anomaly (and removal if necessary) the transport system 114 can be restarted, and method 300 returns to 302, resuming normal operations.

Figure 4:
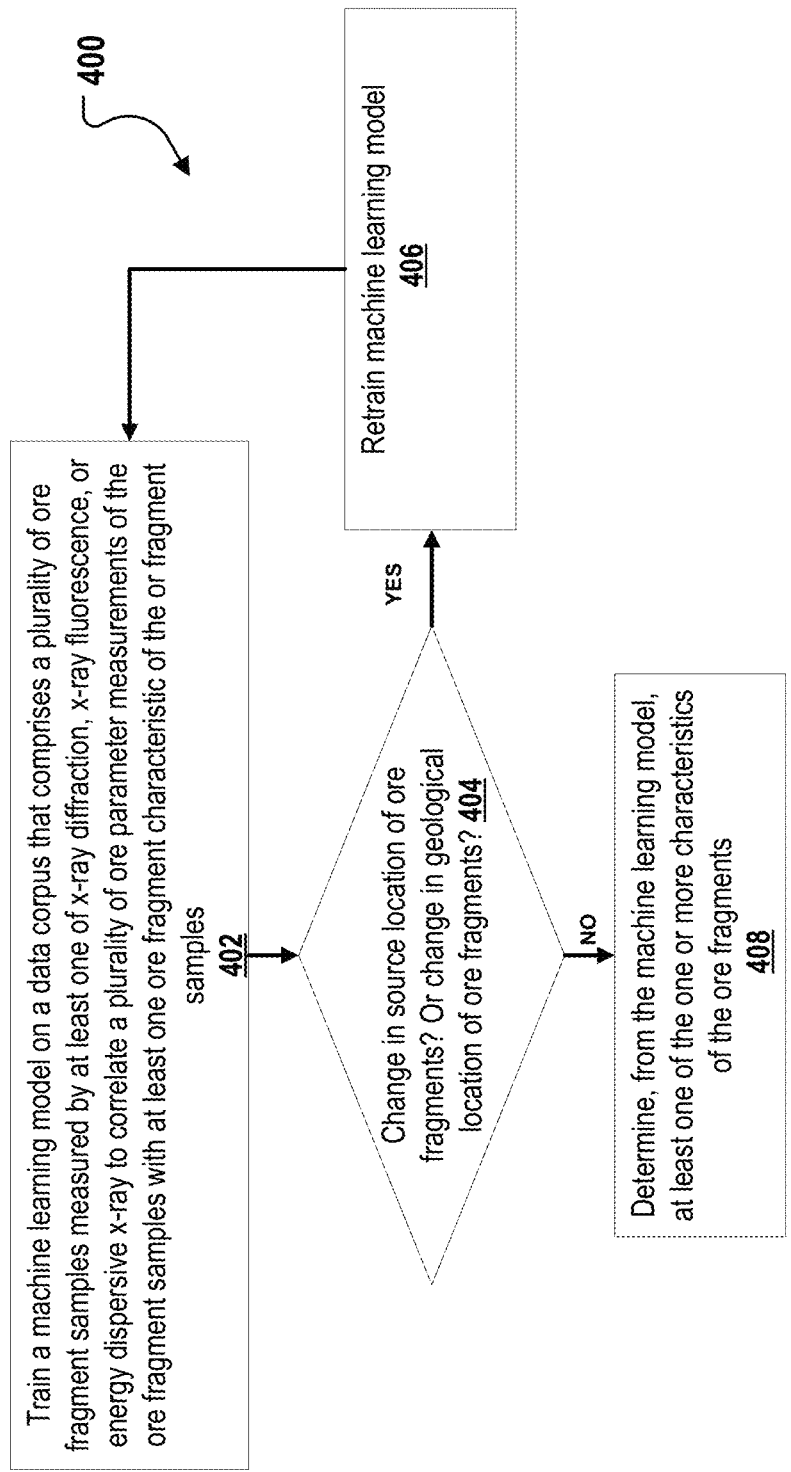
FIG. 4 is a flowchart illustrating an example method for training a machine learning system to determine ore characteristics in an ore composition imaging system.

FIG. 4 is a flowchart illustrating an example method for training a machine learning system to determine ore characteristics in an ore composition imaging system. For clarity of presentation, the description that follows generally describes method 400 in the context of the other figures in this description. However, it will be understood that method 400 can be performed, for example, by any system, environment, software, and hardware, or a combination of systems, environments, software, and hardware, as appropriate. In some implementations, various steps of method 400 can be run in parallel, in combination, in loops, or in any order.

Method 400 begins at 402. A machine learning model is trained using a data corpus of XRD, XRF, or EDS images of ore fragments. The machine learning model is then able to measure one or more parameters of the ore fragments from the images. Ore fragments in the data corpus can have one or more known characteristics, which can then be correlated by the machine learning model with the one or more measured parameters. The training effectiveness can be determined using additional data containing images ore fragments with known characteristics, and determining if the machine learning model is able to accurately determined the characteristics. Once it is determined that the machine learning model is effectively able to correlate characteristics of the ore with measured parameters, method 400 proceeds to step 404.

At step 404 a determination is made whether or not there has been a change in the ore fragments, and if retraining of the machine learning model is required. For example, if the ore fragments being imaged are from a new source location (e.g., different area in the mine, or different geological layer), they may not have the same measurable parameters, or exhibit the same patterns as the data corpus used to train the machine learning model. In another example, if the ore entering the ore processing facility may be from a different geological location (e.g., a different mine, or a different type of ore). If it is determined that there is a change in the ore fragments, or that the machine learning model needs to be retrained, method 400 proceeds to step 406. If there has not been a change in the ore fragments, and the machine learning model does not need retraining, method 400 proceeds to 408.

At 408 the machine learning model determines one or more characteristics of the ore fragments. These determined characteristics can then be readily displayed to a user on a computing device, or used as input to change an operating parameter or mode of operation of the processing facility. In one implementation the system can detect anomalous pieces of ore, and stop a conveyor belt, to allow for further inspection, or to prevent damage to equipment. The determined characteristics can be, but are not limited to the mineral composition, density, porosity, fracture type, fragment size, moisture content, surface composition and hardness.

Returning to 404, if it was determined that the machine learning model needs to be retrained, method 400 proceeds to step 406. At 406, the machine learning model is retrained. Method 400 returns to step 402, and training begins again. The retraining of the machine learning model can include the original data corpus, or a new data corpus or a combination thereof.

Figure 5:
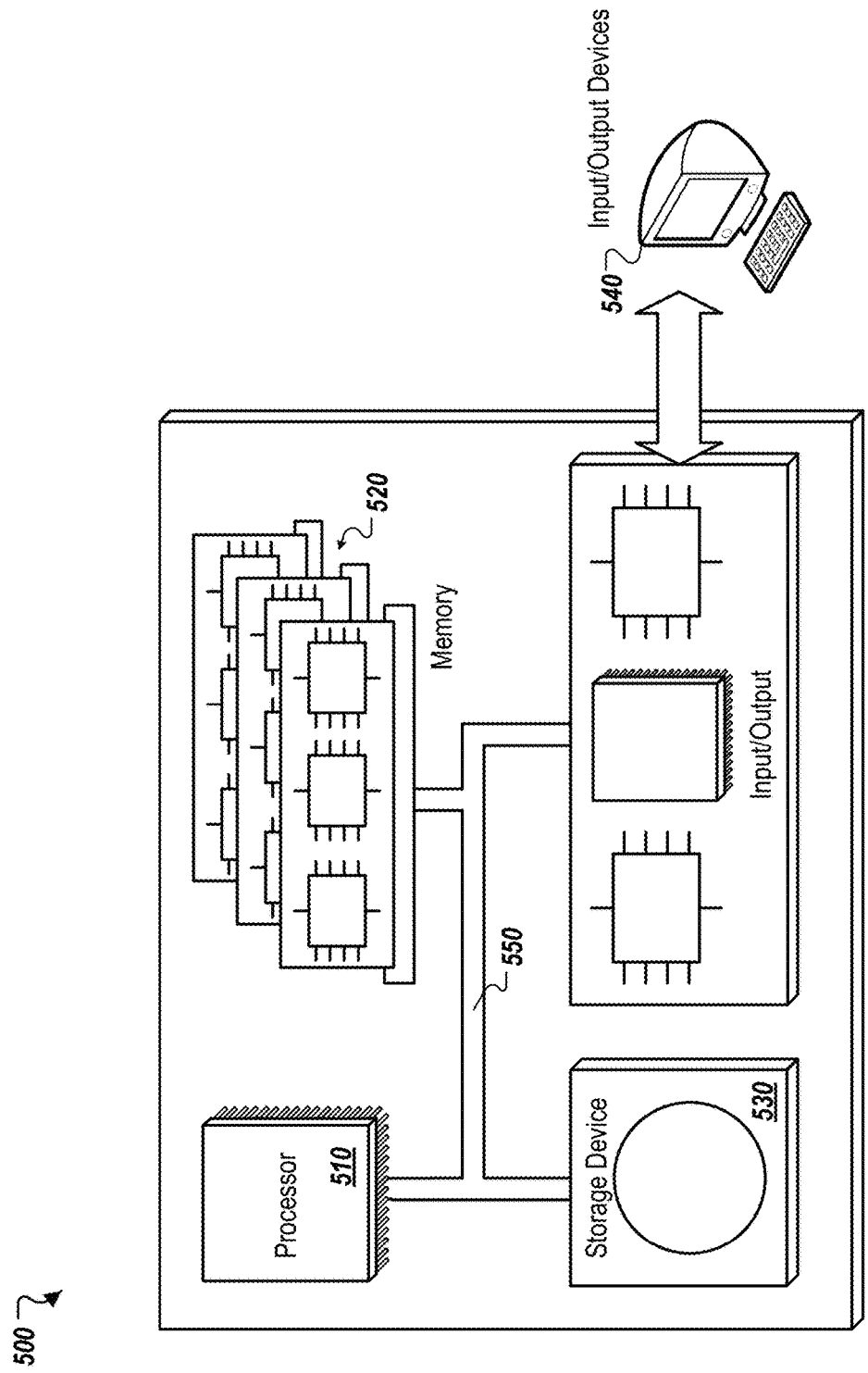
FIG. 5 depicts a computing system for an ore processing facility that includes an ore composition imaging system.

FIG. 5 is a schematic diagram of a computer system 500. The system 500 can be used to carry out the operations described in association with any of the computer-implemented methods described previously, according to some implementations. In some implementations, computing systems and devices and the functional operations described in this specification can be implemented in digital electronic circuitry, in tangibly-embodied computer software or firmware, in computer hardware, including the structures disclosed in this specification (e.g., computing system 108) and their structural equivalents, or in combinations of one or more of them. The system 500 is intended to include various forms of digital computers, such as laptops, desktops, workstations, personal digital assistants, servers, blade servers, mainframes, and other appropriate computers. The system 500 can also include mobile devices, such as personal digital assistants, cellular telephones, smartphones, and other similar computing devices. Additionally, the system can include portable storage media, such as, Universal Serial Bus (USB) flash drives. For example, the USB flash drives may store operating systems and other applications. The USB flash drives can include input/output components, such as a wireless transducer or USB connector that may be inserted into a USB port of another computing device.

The system 500 includes a processor 510, a memory 520, a storage device 530, and an input/output device 540. Each of the components 510, 520, 530, and 540 are interconnected using a system bus 550. The processor 510 is capable of processing instructions for execution within the system 500. The processor may be designed using any of a number of architectures. For example, the processor 510 may be a CISC (Complex Instruction Set Computers) processor, a RISC (Reduced Instruction Set Computer) processor, or a MISC (Minimal Instruction Set Computer) processor.

In one implementation, the processor 510 is a single-threaded processor. In another implementation, the processor 510 is a multi-threaded processor. The processor 510 is capable of processing instructions stored in the memory 520 or on the storage device 530 to display graphical information for a user interface on the input/output device 540.

The memory 520 stores information within the system 500. In one implementation, the memory 520 is a computer-readable medium. In one implementation, the memory 520 is a volatile memory unit. In another implementation, the memory 520 is a non-volatile memory unit.

The storage device 530 is capable of providing mass storage for the system 500. In one implementation, the storage device 530 is a computer-readable medium. In various different implementations, the storage device 530 may be a floppy disk device, a hard disk device, an optical disk device, or a tape device.

The input/output device 540 provides input/output operations for the system 500. In one implementation, the input/output device 540 includes a keyboard and/or pointing device. In another implementation, the input/output device 540 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits). The machine learning model can run on Graphic Processing Units (GPUs) or custom machine learning inference accelerator hardware.

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Additionally, such activities can be implemented via touch-screen flat-panel displays and other appropriate mechanisms.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

What is claimed is:

1. An ore processing system, comprising:
   one or more processors; and
   one or more tangible, non-transitory media operably connectable to the one or more processors and storing instructions that, when executed, cause the one or more processors to perform operations comprising:
      causing an imaging capture system to record a plurality of images of a stream of ore fragments en route from a first location in an ore processing facility to a second location in the ore processing facility;
      correlating the plurality of images of the stream of ore fragments with one or more characteristics of the ore fragments using a machine learning model that comprises a plurality of ore parameter measurements associated with the one or more characteristics of the ore fragments;
      determining, based on the correlation, at least one of the one or more characteristics of the ore fragments;
      generating, for display on a user computing device, data indicating the one or more characteristics of the ore fragments or data indicating an action or decision based on the one or more characteristics of the ore fragments; and
      causing a change to a chemical composition of a froth flotation system of the ore processing facility based on the determined one or more characteristics of the ore fragments.

2. The system of claim 1, wherein the plurality of images comprise:
   images comprising layers of red, green, blue, and grey;
   hyperspectral images;
   acoustic images;
   gravimetric images; or
   depth imagery images.

3. The system of claim 1, wherein the machine learning model comprises an artificial neural network.

4. The system of claim 1, wherein the plurality of ore parameter measurements comprise measurements based on at least one of x-ray diffraction (XRD), x-ray fluorescence (XRF), or energy dispersive x-ray (EDS).

5. The system of claim 1, wherein the one or more characteristics comprises at least one of mineral composition, density, porosity, fracture type, fragment size, fragment moisture content, or hardness.

6. The system of claim 1, wherein the operations further comprise:
   based on the determined one or more characteristics of the ore fragments, adjusting an operation of the ore processing facility.

7. The system of claim 6, wherein adjusting an operation of the ore processing facility comprises at least one of:
   causing a change of route of the stream of ore fragments from the first location in the ore processing facility to a third location in the ore processing facility different than the second location; or
   causing an adjustment of an ore source of the stream of ore fragments moving through the ore processing facility.

8. The system of claim 1, further comprising an electromagnetic (EM) imaging system, the operations further comprising:
   causing the EM imaging system to record a plurality of EM images of the stream of ore fragments moving from the first location in the ore processing facility to the second location in the ore processing facility; and
   determining, based on the plurality of EM images, one or more mineral characteristics of the ore fragments.

9. The system of claim 8, wherein the one or more mineral characteristics comprises at least one of ore fragment density, ore fragment size, or ore fragment surface composition.

10. The system of claim 1, wherein the operations further comprise:
    determining, based on at least one of the plurality of images, an anomaly within the stream of ore fragments; and
    based on the determination of the anomaly, causing a change to an operation of the ore processing facility.

11. The system of claim 10, wherein the change to the operation of the ore processing facility comprises causing a stop to a movement of the stream of ore fragments en route from the first location in the ore processing facility to the second location in the ore processing facility.

12. The system of claim 1, wherein causing the imaging capture system to record the plurality of images of the stream of ore fragments en route from the first location in the ore processing facility to the second location in the ore processing facility comprises:
    causing the imaging capture system to record the plurality of images of the stream of ore fragments as the ore fragments are moving from the first location in the ore processing facility to the second location in the ore processing facility.

13. The system of claim 12, wherein causing the imaging capture system to record the plurality of images of the stream of ore fragments as the ore fragments are moving from the first location in the ore processing facility to the second location in the ore processing facility comprises:
    causing the imaging capture system to record the plurality of images of the stream of ore fragments as the ore fragments are moving on a conveyor or belt continuous feed system from the first location in the ore processing facility to the second location in the ore processing facility.

14. The system of claim 1, wherein the machine learning model is trained on a data corpus that comprises a plurality of ore fragment samples measured by at least one of x-ray diffraction (XRD), x-ray fluorescence (XRF), or energy dispersive x-ray (EDS) to correlate a plurality of ore parameter measurements of the ore fragment samples with at least one ore fragment characteristic of the ore fragment samples.

15. The system of claim 14, wherein the trained machine learning model is retrainable based on at least one of: a change in source location of the ore fragments in the stream of ore fragments, or a change in geological location of the ore fragments in the stream of ore fragments.

16. The system of claim 1, wherein the ore fragments are pretreated with an imaging enhancement prior to the recording of the plurality of images.

17. A computer-implemented ore processing method executed by one or more processors, the method comprising:
    causing an imaging capture system to record a plurality of images of a stream of ore fragments en route from a first location in an ore processing facility to a second location in the ore processing facility;

correlating the plurality of images of the stream of ore fragments with at least one or more characteristics of the ore fragments using a machine learning model that comprises a plurality of ore parameter measurements associated with the one or more characteristics of the ore fragments;

determining, based on the correlation, at least one of the one or more characteristics of the ore fragments;

generating, for display on a user computing device, data indicating the one or more characteristics of the ore fragments or data indicating an action or decision based on the one or more characteristics of the ore fragments; and causing a change to a chemical composition of a froth flotation system of the ore processing facility based on the determined one or more characteristics of the ore fragments.

18. The method of claim 17, wherein the plurality of images comprise:

images comprising layers of red, green, blue, and grey;
hyperspectral images;
acoustic images;
gravimetric images; or
depth imagery images.

19. The method of claim 17, wherein the machine learning model comprises an artificial neural network.

20. The method of claim 17, wherein the plurality of ore parameter measurements comprise measurements based on at least one of x-ray diffraction (XRD), x-ray fluorescence (XRF), or energy dispersive x-ray (EDS).

21. The method of claim 17, wherein the one or more characteristics comprises at least one of mineral composition, density, porosity, or hardness.

22. The method of claim 17, further comprising based on the determined one or more characteristics of the ore fragments, adjusting an operation of the ore processing facility.

23. The method of claim 22, wherein adjusting an operation of the ore processing facility comprises at least one of:

causing a change of route of the stream of ore fragments from the first location in the ore processing facility to a third location in the ore processing facility different than the second location; or causing an adjustment of an ore source of the stream of ore fragments moving through the ore processing facility.

24. The method of claim 17, further comprising:

causing an electromagnetic (EM) imaging system to record a plurality of EM images of the stream of ore fragments moving from the first location in the ore processing facility to the second location in the ore processing facility; and determining, based on the plurality of EM images, one or more mineral characteristics of the ore fragments.

25. The method of claim 24, wherein the one or more mineral characteristics comprises at least one of ore fragment density, ore fragment size, or ore fragment surface composition.

26. The method of claim 17, further comprising:

determining, based on at least one of the plurality of images, an anomaly within the stream of ore fragments; and based on the determination of the anomaly, causing a change to an operation of the ore processing facility.

27. The method of claim 26, wherein the change to the operation of the ore processing facility comprises causing a stop to movement of the ore stream en route from the first location in the ore processing facility to the second location in the ore processing facility.

28. The method of claim 17, wherein causing the imaging capture system to record the plurality of images of the stream of ore fragments en route from the first location in the ore processing facility to the second location in the ore processing facility comprises:

causing the imaging capture system to record the plurality of images of the stream of ore fragments as the ore fragments are moving from the first location in the ore processing facility to the second location in the ore processing facility.

29. The method of claim 28, wherein causing the imaging capture system to record the plurality of images of the stream of ore fragments as the ore fragments are moving from the first location in the ore processing facility to the second location in the ore processing facility comprises:

causing the imaging capture system to record the plurality of images of the stream of ore fragments as the ore fragments are moving on a conveyor or belt continuous feed system from the first location in the ore processing facility to the second location in the ore processing facility.

30. The method of claim 17, wherein the machine learning model is trained on a data corpus that comprises a plurality of ore fragment samples measured by at least one of x-ray diffraction (XRD), x-ray fluorescence (XRF), or energy dispersive x-ray (EDS) to correlate a plurality of ore parameter measurements of the ore fragment samples with at least one ore fragment characteristic of the ore fragment samples.

31. The method of claim 30, wherein the trained machine learning model is retrainable based on at least one of: a change in source location of the ore fragments in the stream of ore fragments, or a change in geological location of the ore fragments in the stream of ore fragments.

32. The method of claim 17, wherein the ore fragments are pretreated with an imaging enhancement prior to the recording of the plurality of images.

33. A non-transitory computer readable storage medium storing instructions that, when executed by at least one processor, cause the at least one processor to perform operations comprising:

causing an imaging capture system to record a plurality of images of a stream of ore fragments en route from a first location in an ore processing facility to a second location in the ore processing facility;

correlating the plurality of images of the stream of ore fragments with at least one or more characteristics of the ore fragments using a machine learning model that comprises a plurality of ore parameter measurements associated with the one or more characteristics of the ore fragments;

determining, based on the correlation, at least one of the one or more characteristics of the ore fragments;

generating, for display on a user computing device, data indicating the one or more characteristics of the ore fragments or data indicating an action or decision based on the one or more characteristics of the ore fragments; and causing a change to a chemical composition of a froth flotation system of the ore processing facility based on the determined one or more characteristics of the ore fragments.

34. An ore processing system, comprising:
one or more processors; and one or more tangible, non-transitory media operably connectable to the one or more processors and storing instructions that, when executed, cause the one or more processors to perform operations comprising:
causing an imaging capture system to record a plurality of images of a stream of ore fragments en route from a first location in an ore processing facility to a second location in the ore processing facility;
correlating the plurality of images of the stream of ore fragments with one or more characteristics of the ore fragments using a machine learning model that comprises a plurality of ore parameter measurements associated with the one or more characteristics of the ore fragments;
determining, based on the correlation, at least one of the one or more characteristics of the ore fragments;
determining, based on at least one of the plurality of images, an anomaly within the stream of ore fragments;
based on the determination of the anomaly, causing a change to an operation of the ore processing facility comprising a stop to a movement of the stream of ore fragments en route from the first location in the ore processing facility to the second location in the ore processing facility; and
generating, for display on a user computing device, data indicating the one or more characteristics of the ore fragments or data indicating an action or decision based on the one or more characteristics of the ore fragments.

* * * * *